(12) United States Patent
Lever et al.

(10) Patent No.: US 10,959,661 B2
(45) Date of Patent: Mar. 30, 2021

(54) QUANTIFICATION OF BULBAR FUNCTION

(71) Applicant: The Curators of the University of Missouri, Columbia, MO (US)

(72) Inventors: Teresa Lever, Columbia, MO (US); Filiz Bunyak Ersoy, Columbia, MO (US); Mili Kuruvilla-Dugdale, Columbia, MO (US); Yunxin Zhao, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 471 days.

(21) Appl. No.: 15/945,936

(22) Filed: Apr. 5, 2018

(65) Prior Publication Data

US 2018/0289308 A1 Oct. 11, 2018

Related U.S. Application Data

(60) Provisional application No. 62/481,946, filed on Apr. 5, 2017.

(51) Int. Cl.
*A61B 5/00* (2006.01)
*A61B 5/11* (2006.01)
(Continued)

(52) U.S. Cl.
CPC .......... *A61B 5/4082* (2013.01); *A61B 5/0077* (2013.01); *A61B 5/1124* (2013.01);
(Continued)

(58) Field of Classification Search
CPC ... A61B 5/4082; A61B 5/1124; A61B 5/7282; A61B 5/4803; A61B 5/4205; A61B 5/0077; A61B 5/1128; A61B 5/4884; G06K 9/00711; G06K 9/00315; G06K 2009/00738; G10L 25/66; G10L 2015/027
See application file for complete search history.

(56) References Cited

U.S. PATENT DOCUMENTS

| | | | |
|---|---|---|---|
| 2008/0165707 A1* | 7/2008 | Baird | H04L 65/605 370/260 |
| 2011/0066068 A1* | 3/2011 | Duffy | G16H 40/63 600/558 |

FOREIGN PATENT DOCUMENTS

EP 2394574 A1 * 12/2011 ........... A61B 5/0064

OTHER PUBLICATIONS

Panying Rong et. al., "Predicting Early Bulbar Decline in Amyotrophic Lateral Sclerosis: A Speech Subsystem Approach", Hindawi Publishing Corporation (Year: 2015).*

(Continued)

*Primary Examiner* — Eric F Winakur
*Assistant Examiner* — Abid A Mustansir
(74) *Attorney, Agent, or Firm* — Erise IP, P.A.

(57) ABSTRACT

System, method and media for quantifying bulbar function of a subject. At a high level, embodiments of the invention measure and quantify bulbar function of a test subject based on video data, audio data, or other sensor data of a subject performing a test of bulbar function, such as speech, swallowing, and orofacial movements. This sensor data is then analyzed to identify key events such as syllable enunciations. Based on one or more characteristics of these key events (such as, for example, their rate, count, assessed accuracy, or trends over time), the bulbar function of the subject can accurately, reliably, and objectively be quantified.

20 Claims, 3 Drawing Sheets

(51) Int. Cl.
*G06K 9/00* (2006.01)
*G10L 25/66* (2013.01)
*G10L 15/02* (2006.01)

(52) U.S. Cl.
CPC .......... *A61B 5/4205* (2013.01); *A61B 5/4803* (2013.01); *A61B 5/7282* (2013.01); *G06K 9/00315* (2013.01); *G06K 9/00711* (2013.01); *G10L 25/66* (2013.01); *A61B 5/1128* (2013.01); *A61B 5/4884* (2013.01); *G06K 2009/00738* (2013.01); *G10L 2015/027* (2013.01)

(56) References Cited

OTHER PUBLICATIONS

Cheng-Chieh Yang, et. al. "Analysis of verbal diadochokinesis in normal speech using the diadochokinetic rate analysis program", Journal of Dental Science (Year: 2011).*

Soo-Eun Chang, et. al., "Common neural substrates support speech and non-speech vocal tract gestures", Neuroimage (Year: 2009).*

* cited by examiner

QUANTIFICATION OF BULBAR FUNCTION

RELATED APPLICATION

This non-provisional patent application claims priority benefit, with regard to all common subject matter, of earlier-filed U.S. Provisional Patent Application No. 62/481,946 filed Apr. 5, 2017 and entitled "Detecting and Monitoring Bulbar Dysfunction." The identified earlier-filed provisional patent application is hereby incorporated by reference in its entirety into the present application.

BACKGROUND

1. Field

Embodiments of the invention generally relate to the automated analysis and quantification of bulbar function and, more particularly, to the detection and monitoring of bulbar dysfunction.

2. Related Art

Traditionally, when analyzing orofacial dexterity and related bulbar function (e.g., sensori-motor functions of the head and neck, particularly those involved in speech, facial expression, and swallowing processes), evaluation of function and dysfunction has been a subjective determination by a medical professional. For example, a speech-language pathologist may ask a patient to produce or repeat a particular sound or phrase as quickly as possible, and estimate oral-motor skills based on the ability of the patient to comply. However, the results of such testing can be difficult to quantify accurately and diagnosis is, of a necessity, subjective. Testing in this way produces inconsistent diagnoses, even in putatively objective testing, as a result of a lack of inter-rater reliability. Additionally, subjectivity is present in the putatively objective testing due to inconsistency in the variables observed, as no solution exists that analyzes a comprehensive set of variables pertaining to bulbar function.

As such, what is needed is a way to automatically and reliably quantify bulbar function so that any change in function can be quickly detected. This shifts measurement of bulbar function from a subjective, qualitative evaluation to an objective, quantitative one. The ability to objectively measure bulbar function allows it to be used as a diagnostic tool for detecting and diagnosing a wide variety of temporary, permanent, and chronic conditions, as well as the ability to track the progression of such conditions when they are diagnosed. Furthermore, automated quantification of function and dysfunction can be used to track compliance with prescribed therapy and provide a patient with feedback to enhance practice accuracy. One embodiment of the therapy is speech therapy, which targets speech and swallowing function, as well the various orofacial movements that are essential to these functions.

SUMMARY

Embodiments of the invention address the above-described need by providing for a system to automatically, objectively and reliably quantify bulbar function. In particular, in a first embodiment, the invention includes a system for quantifying bulbar function, comprising at least one sensor configured to capture data of a subject performing a test of bulbar function, a processor, one or more non-transitory computer-readable media storing computer-executable instructions that, when executed by the processor, perform a method of quantifying bulbar function in the subject based on the test, comprising the steps of receiving, from the sensor, the captured data of the subject performing the test of the bulbar function, identifying, based on the captured data, a plurality of key events, calculating, based on the plurality of key events, a functional quantification of bulbar function for the subject.

In a second embodiment, the invention includes a method of quantifying bulbar function for a subject, comprising the steps of presenting, to the subject, a task testing the subject's bulbar function, receiving, from a sensor, data of the subject performing the task, identifying, in the data, a plurality of key events, calculating, for each key event of the plurality of key events, a quantification for the key event to obtain a respective plurality of key event quantifications, determining, based on the plurality of key event quantifications, a functional quantification of the subject's bulbar function, and presenting, to the subject, the functional quantification.

In a third embodiment, the invention includes one or more non-transitory computer-readable media storing computer-executable instructions that, when executed by a processor, perform a method of quantifying bulbar function for a subject, the method including steps of receiving data from a sensor of the subject performing a task testing the subject's bulbar function, identifying, in the received data, a plurality of key events, determining, based on the identified key events, a rate of key events during a predetermined time interval of the task, and determining, based on the rate of key events, a functional quantification of the subject's bulbar function.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

At a high level, embodiments of the invention measure and quantify bulbar function of a test subject based on video data, audio data, or other sensor data of a subject performing a test of bulbar function, such as speech (to measure function of the lips, tongue, and throat) or mastication (to measure function of the masseter and tongue muscles). Other functions, such as swallowing and facial expression for communication, may also be measured and quantified in other applications. Such quantification can be useful where bulbar function is an existing diagnostic measure. For example, Parkinson's Disease and Amyotrophic Lateral Sclerosis (ALS) can involve speech and swallowing impairment even in pre-clinical stages, and early diagnosis significantly improves the prognosis for these diseases. As such, early detection and monitoring of bulbar dysfunction can significantly improve outcomes of these and other age-related neurological disorders.

Furthermore, where measurement is easy, accurate, and reliable, bulbar function can be used as a diagnostic measure where it was not previously available. For example, a change in bulbar function after a head injury could be indicative of a concussion. Similarly, degraded bulbar function by an operator of a motor vehicle may indicate impairment by alcohol or drugs. A change in bulbar function before as compared to after a treatment (such as dental surgery or radiation therapy for oral cancer) can be used to measure the effectiveness or side effects of the treatment. Alternatively, quantification of bulbar function can be useful in training any sort of vocal performance. For example, singers or students of a foreign language can receive feedback on how closely their performance matches an ideal.

The subject matter of embodiments of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be obvious to one skilled in the art, and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments, but is not necessarily included. Thus, the technology can include a variety of combinations and/or integrations of the embodiments described herein.

Figure 1:
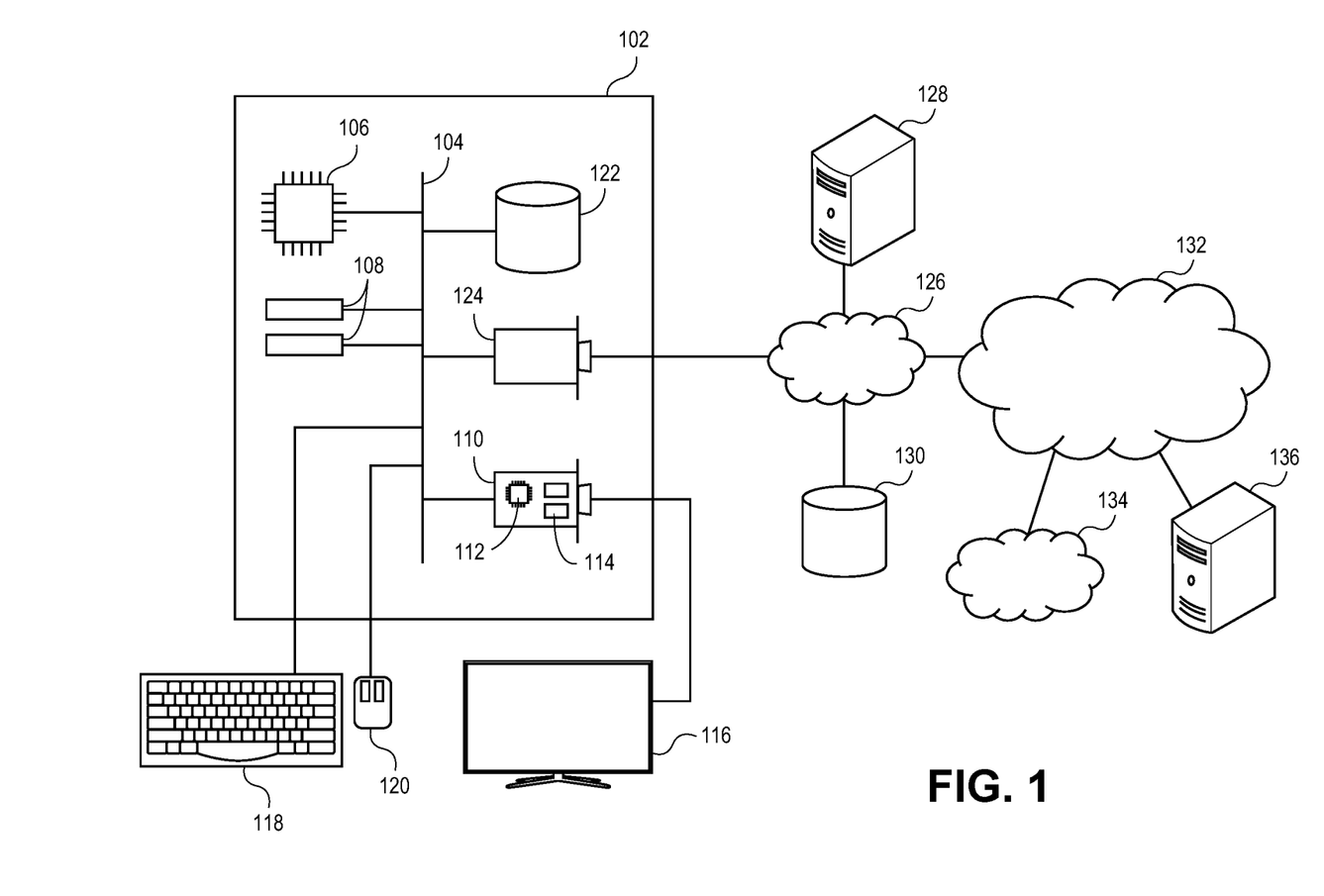
FIG. 1 depicts an exemplary hardware platform for certain embodiments of the invention.

Turning first to FIG. 1, an exemplary hardware platform for certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 104 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-usable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
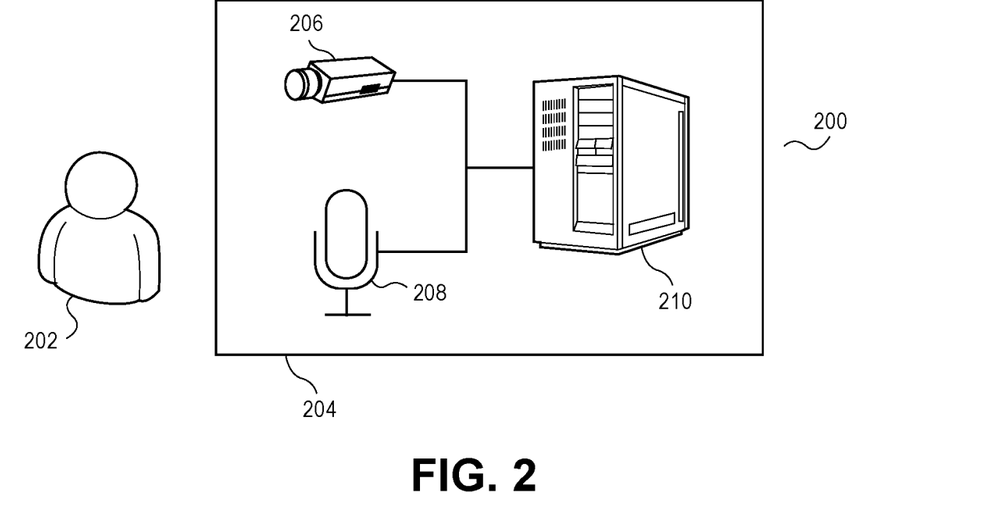
FIG. 2 depicts a block diagram illustrating certain components of a particular embodiment of the invention.

Turning now to FIG. 2, a block diagram illustrating certain components of a particular embodiment of the invention is depicted and referred to generally by reference numeral 200. Subject 202 is being examined by system 204. In some embodiments, subject 202 is a patient being examined in the process of diagnosis or treatment. For example, system 204 can be used in the early detection of age-related neurological disorders such as Parkinson's Disease and Amyotrophic Lateral Sclerosis (ALS) or neurological injuries such as concussions. In other embodiments, subject 202 is a patient undergoing comparative pre- and post-treatment function testing. For example, bulbar function may be tested before and after radiation treatment for oral cancer. Similarly, system 204 may be performing outcome analysis after dental surgery. In still other embodiments, system 204 is performing antagonistic testing such as sobriety testing for subject 202. Broadly speaking, embodiments of the invention contemplate any scenario where quantification of bulbar function is a useful indication.

As such, system 204 may take a variety of forms depending on application. As depicted, system 204 includes camera 206, microphone 208, and processor 210. However, system 204 may include more components or fewer. For example, in some embodiments, system 204 may include a display. In other embodiments, system 204 may omit camera 206 and/or microphone 208. In still other embodiments, a first device may include sensors for gathering data on bulbar function (such as camera 206 and microphone 208) while a second device may include the processor 210 for analyzing the data. The results of the analysis may be presented on either device or a separate, third device. In one exemplary embodiment, system 204 can be implemented on a smartphone used by subject 202. In another embodiment, system 202 can be implemented on a dedicated device with integrated sensors and signal processing. In still other embodiments, system 204 can be implemented on a conventional desktop computer with attached peripherals.

Camera 206 may be any form of camera oriented so as to capture imagery of part or all of the head, face, and neck region of subject 202, and may capture black-and-white or color imagery. In some embodiments, camera 206 is a conventional digital video camera that captures imagery at 23.976, 24, 25, 29.97, 30, 50, 59.94, or 60 frames per second. In other embodiments, camera 206 is a still camera that captures still images. In still other embodiments, camera 206 is a high-speed video camera that captures images at a rate of 250, 1000, or more frames per second. In some embodiments, camera 206 is operable to capture three-dimensional imagery of subject 202. In other embodiments, camera 206 captures non-visible spectrum (e.g., infra-red) imagery of subject 202. In some embodiments, system 204 may include a projector operable to generate a pattern in a visible or non-visible spectrum that can be captured by camera 206 to ascertain depth information.

Microphone 208 may broadly be any form of audio input device and may be analog or digital. In some embodiments, microphone 208 is a conventional microphone associated with a smartphone of subject 202. In other embodiments microphone 208 is a dedicated peripheral optimized to create high-quality audio. In some embodiments, microphone 208 captures audio data at approximately 5-8 kHz. In other embodiments, microphone 208 captures audio data at approximately 20 kHz or 44 kHz so as to capture supra-vocal frequency ranges for increased diagnostic utility. In still other embodiments, microphone 208 captures at a sample rate of approximately 96 kHz, 192 kHz or higher. Similarly, microphone 208 can capture audio data at a bit depth of 8, 16, 24, or 32 bits per sample. In some embodiments, audio data may be captured at other bit depths as well.

Processor 210 functions to process the video data from camera 206, the audio data from microphone 208 and/or data from any other sensors of system 204, as described in greater detail below. In some embodiments, processor 210 is a dedicated digital signal processor as implemented on an ASIC or an FPGA. In other embodiments, processor 210 is a conventional microprocessor or microcontroller as described above with respect to FIG. 1. For example, in the embodiment described above where system 204 is implemented on a smartphone of subject 202, processor 210 may be the processor of that smartphone. Broadly, any processor operable to perform the processing functions described herein is contemplated as being within the scope of the invention.

Figure 3:
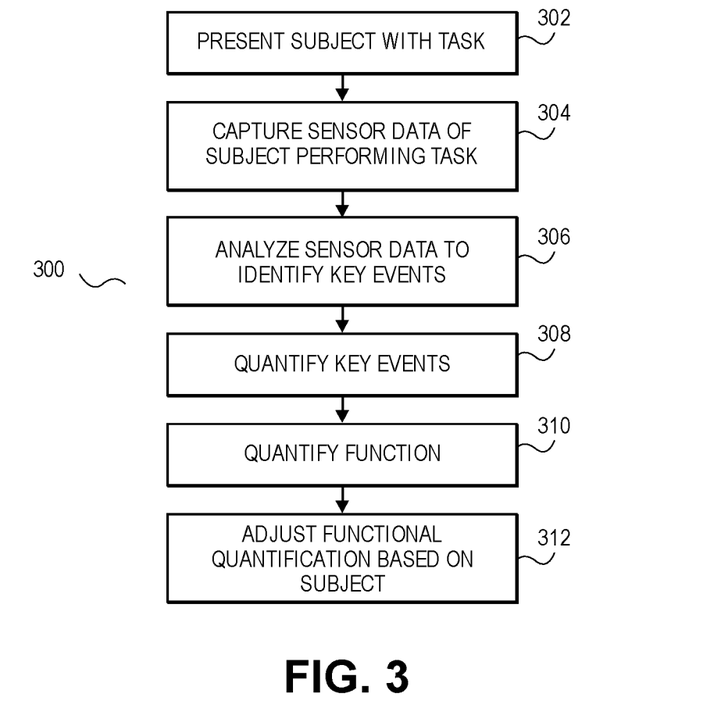
FIG. 3 depicts a flowchart depicting the operation of a method in accordance with embodiments of the invention.

Turning now to FIG. 3, a flowchart depicting the operation of a method in accordance with embodiments of the invention is depicted and generally referred to by reference numeral 300. Initially, at step 302, the subject is presented with a task. In some embodiments, tasks are presented via a display integrated into system 204. In other embodiments, tasks are assigned by a doctor or other party in charge of administering the test. In still other embodiments, tasks are assigned by another party, but subject 202 administers the test themselves via (for example) their smartphone.

Broadly, the task can be any measure of bulbar function to assess neurological or sensori-motor function. Generally speaking, these tasks are designed to challenge the subject, and the performance of even healthy, unaffected subjects may break down. However, the performances of healthy subjects and affected subjects break down differently, and different pathologies break down differently from each other. As an example, in order to assess speech function, the subject may be tasked with rapidly producing alternating sounds. Such a test may be referred to as measuring the subject's diadochokinetic (DDK) rate. In a DDK rate test, the subject may be instructed to repeat a single syllable (such as "puh"), a series of syllables (such as "puh-tuh-kuh"), or a word containing appropriate syllables (such as "pattycake" or "buttercup") as quickly and accurately as possible. Such tests require distinct placements of the tongue and other bulbar structures (e.g., lips, soft palate, etc.) and, as such, can detect various pathologies involving dysfunction of these structures. Another example of a task that may be presented to the subject is a novel "tongue tick rate test," where the subject is tasked with repeating a "tick" sound as quickly as possible. Other specific tasks for assessing other measures of bulbar function are also contemplated as being within the scope of the invention.

In particular, mastication and swallowing tasks are also contemplated to evaluate swallowing function (and bulbar function more generally). For example, subject 202 may be tasked with chewing and swallowing a dry, hard, crunchy food such as pretzels to diagnose dysphagia. Similarly, subject 202 may be tasked with tasked with swallowing a predetermined amount (such as 100 mL) of water as quickly as possible, with a swallow rate below a pre-determined threshold (for example, below 10 mL per second) being indicative of dysphagia. Certain tasks may simply require the subject to perform particular facial expressions or movements and, as such, can be assessed using only video data (as discussed in greater detail below). For example, in order to measure craniomotor nerve function, the subject may be tasked with smiling, puckering the lips, or opening their eyes as wide as possible.

Next, at step 304, one or more sensors of system 204 capture data of subject 202 performing the assigned task. One of skill in the art will appreciate that each sensor captures its own respective data set of the performance. For example, microphone 208 may capture audio data of the task, while camera 206 may capture video of the subject's head, neck and/or face as they perform the task. In some embodiments, this data may be stored directly for analysis. In other embodiments, it may be pre-processed prior to storage. For example, if camera 206 is capturing data on the facial movements of subject 202, the video data may be stored or the data may be processed to identify key facial points which can tracked, and the tracking data may be stored instead of the video data. In some embodiments, facial data may be stored using Facial Action Coding System taxonomy. In particular, for some embodiments, both audio and video (and, optionally, supplemental sensor data) are captured simultaneously for more accurate quantification of bulbar function, as discussed in additional detail below.

Figure 4:
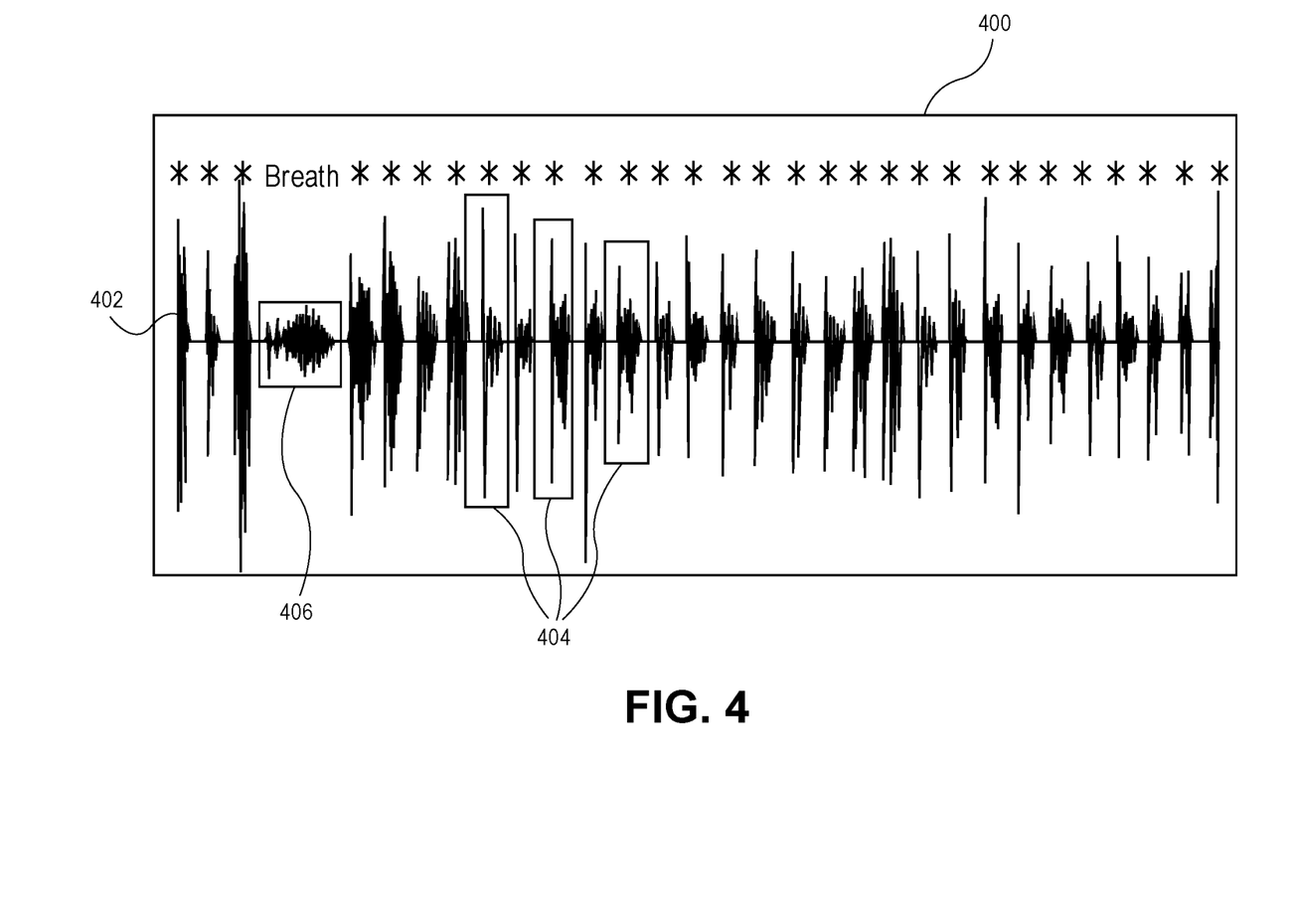
FIG. 4 depicts a sample set of audio data from a microphone collected in accordance with embodiments of the invention.

Processing then proceeds to step 306, where the sensor data is analyzed, to identify key events. For example, if the task is a DDK test, then the key events may be the enunciation of individual syllables. Other types of tests may have different key events. For example, in a mastication test, the key event may be individual chews and swallows, and in a swallowing test, the key event may be the individual swallows. For audio data, these key events may be identified by applying different filters to the audio signal and locating local maxima in the amplitude of an audio signal, or by locating such local maxima above a cutoff threshold. As another example, where the sensor data is facial image or video data, some embodiments may detect the subject's face within a single image or set of images and detect facial landmarks (or components) such as the lips or eyes using computer vision and machine learning techniques. Such techniques may involve deep learning methods such as convolutional neural networks trained to recognize these facial landmarks, or other classical computer vision and/or machine learning algorithms trained to detect facial landmarks relying on appearance or motion of these landmarks. When dynamic analysis is done, some embodiments may treat positions of the facial landmarks/components (or their parts, such as the top-most, left-most corner of lips) as temporal signals. These position signals can be independently processed to extract amplitude and frequency based measures for particular facial landmarks. Some embodiments may also compute relations between two or more landmarks (e.g., distances between corner of lips and eyes, ratios between pairs of distances, or angles between sets of three landmark points), treat these as temporal signals, and compute amplitude and frequency based measures for these relationships. Events may be identified by locating the moment when the mouth is at its maximum openness, the lips are at their most pursed, when the lips first open, or by computing various measures of displacement and motion, such as the opening and closing rate of the lips. Besides dynamic events and measurements, facial data can be used to assess static features such as the distance between various facial components and derived features such as symmetry (e.g., left/right) of such distances as an indicator of paralysis. The analysis of the data to locate the key events will vary depending on the type of data as well as the type of task being quantified. As a more concrete example of this process, FIG. 4 depicts the decomposition of audio data from a DDK test into individual events.

One of skill in the art will appreciate that decomposing a continuous stream of sensor data into key events (and, optionally, inter-event periods) may require the use of heuristic algorithms rather than absolute cutoffs. For example, during a tick test, one subject may "tick" more quietly than another, necessitating a low cutoff threshold. However, another user may have louder breaths (which should not be counted as ticks) than the first user's ticks. Accordingly, key events may be primarily identified based on a first criterion (such as an amplitude threshold), with ambiguous values of the first criterion resolved based on a second criterion (such as event duration or the spectrographic energy profile of the event). In other embodiments, a potential key event must satisfy both the first criterion and the second criterion to be classified as a key event.

Next at step 308, in some embodiments, these key events are quantified. One of skill in the art will appreciate that each event can then be quantified in a number of different ways. For example, the peak amplitude corresponding to each syllable can be identified, the duration of each syllable can be measured, and the syllabic frequency can be calculated. The waveform of each syllable can also be compared to a reference waveform for syllable production accuracy. For example, the time required from onset of a syllable until peak amplitude may indicate the ease or difficulty the subject has in making the correct orofacial articulations needed to pronounce the syllable. The recognition accuracy (i.e., how well the accuracy of the subject's reproduction matches their intent) may be determined. For face-tracking data, the accuracy of the stomatognathic articulations (i.e., movements of the teeth, jaws, and associated soft tissues) can be similarly measured to determine the subject's orofacial dexterity. In some embodiments, the quantification combines data from multiple sensors, such as video data for lip function and audio data for tongue function for the same syllable.

Next, at a step 310, a functional quantification is calculated in some embodiments. This score aggregates the analysis of the key events performed at step 308 to provide a single value (or a relatively small number of values such as a peak function value and a fatigue rate). For example, in a mastication test, the number of times the subject chews may be counted based on individual chew events that are performed before the detection of a swallowing event. In some embodiments, average performance over specified intervals is evaluated. For example, the average tick rate over the first five seconds and the last five seconds of a particular interval may be measured and compared to evaluate fatigue. In other cases, frequency based measures can be directly computed from the audio signal, or in the case of facial motion analysis, from displacement signals through signal frequency analysis, without explicitly detecting individual events of interest.

The trends over the course of the task can also be analyzed. For example, the rate of change of the tick rate in a tick rate task may be analyzed to determine a fatigue effect. Similarly, if the amplitude of successive ticks declines, this may indicate fatigue as well. For certain types of data, breaths taken by the subject during the task may be recognized. The frequency, number, or depth of breaths required to complete the task may also be analyzed with the other task data. For speech tasks, the rate and/or rhythm of speech performance may be measured. Similar analysis may be performed for other types of task. As described above, the functional quantification may be based on data from a single sensor or data from a plurality of sensors. The functional quantification may further be based on data from the task assignment. For example, the set of audio data may be quantified differently if the user was assigned to produce a "puh" syllable than if they were assigned to produce a "kuh" syllable.

Finally, at a step 312, the functional score may be adjusted based on the demographic characteristics of subject 202. For example, if the subject is between 60 and 69 years of age, the functional quantification may be increased by a fixed value (or by a fraction of the raw amount) to compensate for normal age-related variances in function. In some embodiments, when the functional quantification is used to diagnose a disorder, different threshold between normal and deficient function are instead used for different demographic groups. The adjusted functional quantification may be compared to baseline population data or to a previous functional quantification for the patient. In some embodiments, different baseline data may be used (or baseline data may be normalized) based on the accent or other speech patterns of the speaker.

In some embodiments, the adjusted functional quantification is presented to test administrator. In other embodiments, the adjusted functional quantification is presented to the subject. In still other embodiments, an outcome of the test (such as a pass/fail or a rating of performance relative to normative values) based on the adjusted functional quantification (or the unadjusted functional quantification) is presented to the test administrator or the subject. In yet other embodiments, the adjusted functional quantification is used to provide the subject with feedback on their execution of the task. This feedback can be related to audio data in the form of accuracy assessments, volume measurements, rhythm, or rate. This feedback can also be related to visual data in the form of symmetry measurements, facial feature movements or position, or movement magnitude. Where visual data is gathered, a demonstration of a correct reference movement may be provided on a display of system 204 as well. Where progression of a degenerative disease or a course of treatment, the subject or a test administrator may be able to see and/or listen to recordings of prior executions of the task as well, or view the qualifications from them.

Turning now to FIG. 4, a sample set of audio data from microphone 208 is depicted and referred to generally by reference numeral 400. As shown, audio data 400 depicts the amplitude 402 of the audio signal over time as subject 202 performs a DDK test. Thus, amplitude data 402 corresponds to the data collected at step 304. The absolute amplitude 402 increases each time subject 202 enunciates a "tuh," with the highest absolute amplitude corresponding to the plosive of the "t." Thus, at step 306, each of these syllable enunciations 404 can be identified as a key event. However, identifying syllables solely based on local absolute maxima can lead to falsely identifying breath 406 as a syllable enunciation.

As such, additional signal and key event features and/or heuristics can be used to distinguish potential false positives such as breath 406 from true positives such as syllable enunciations 404. As can be seen from FIG. 4, the waveform of breaths 406 differs significantly from that of syllable enunciation 404. In order to distinguish between the two of them (and between those and the inter-event periods), differences in peak amplitude, waveform shape, event length, and spectrographic energy distribution (not shown) can be used.

As an example of this process, breath 406 can be distinguished from syllable enunciations 404 by virtue of having a lower peak amplitude. As such, the combined criteria for determining a syllable enunciation may be that the amplitude goes from zero (or near zero) to a peak above a predetermined threshold, and then back to zero or near zero. However, as described above, the threshold between breaths and syllable enunciations may differ from subject to subject, or based on the distance between subject 202 and microphone 208. As such, it may be preferable in this instance to use waveform shape to distinguish breath 406 from syllable enunciations 404. The characteristic shape of a waveform for breath 406 is a slowly increasing amplitude followed by an equally slowly decreasing amplitude. By contrast, the characteristic waveform shape of a "tuh" syllable is a sharp spike in amplitude (corresponding to the plosive) followed by a relatively quick decay. These waveforms are resilient to changes in volume and can therefore be used to distinguish different types of key events in a wide variety of circumstances.

In some embodiments, machine learning can be used to identify key events based on the various features included in the sensor data. For example, embodiments of the invention may employ Hidden Markov Models (HMM) by approximating the sensor data as a piecewise stationary process. In such systems, an event classifier can output a sequence of cepstral coefficients. Each type of key event will tend to have a different output statistical distribution, which can be used to determine the most likely key event for each segment of the sensor data (whether audio data, video data, or other types of sensor data). Alternatively, Artificial Neural Networks (ANN) can be used to identify individual key events such as disconnected phonemes in sensor data. In still other embodiments, ANNs can be used in combination with HMMs to preprocess the data for continuous-time recognition of sensor data (such as speech recognition). In still other embodiments, supervised or unsupervised learning (e.g., clustering) may be used to categorize speech samples.

However, the needs of event identification and matching are distinct from those in conventional speech recognition. In normal speech recognition, it is desirable to ignore the differences between a reference sound form and the user's sound form so as to understand a wide variety of speech. In diagnosing speech pathologies, however, those differences may provide information of high diagnostic utility. Furthermore, in conventional speech recognition tasks, layers of semantics are present that can be used to correct errors in lower recognition layers. For example, sentence-level grammar can be used to disambiguate between homophones, while dictionaries can be used to disambiguate between ambiguous phoneme combinations. When diagnosing speech pathology, only an expected syllable or phoneme is known. As such, entirely new models for machine learning are required for use with embodiments of the present invention.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain

Having thus described various embodiments of the invention, what is claimed as new and desired to be protected by Letters Patent includes the following:

1. A system for quantifying bulbar function, comprising:
a sensor configured to capture data of a subject performing a test of bulbar function;
a processor; and
one or more non-transitory computer-readable media storing computer-executable instructions that, when executed by the processor, perform a method of quantifying bulbar function in the subject based on the test, comprising the steps of:
receiving, from the sensor, the captured data of the subject performing the test of the bulbar function;
identifying, in the captured data, a plurality of key events;
calculating, for each key event of the plurality of key events, a quantification for the key event to obtain a respective plurality of key event quantifications;
calculating, for each key event of the plurality of key events, a fatigue effect for the key event to obtain a respective fatigue rate associated with the plurality of key event quantifications,
wherein the plurality of key events are performances of repetitive sensori-motor functions and the plurality of key key event quantifications are measures of the performances of repetitive sensori-motor functions relative to normative values; and
calculating, based on the plurality of key event quantifications and the fatigue rate, a functional quantification of bulbar function for the subject.

2. The system of claim 1, wherein the method further comprises the step of prompting the subject with a task of the test of bulbar function.

3. The system of claim 1, wherein the sensor is a microphone.

4. The system of claim 3, further comprising an additional sensor configured to capture additional data of the subject performing the test of bulbar function, and wherein the key events are further identified based on the additional captured data.

5. The system of claim 4, wherein the additional sensor is a video camera.

6. The system of claim 1, wherein the quantification of bulbar function for the subject is calculated based on a count of key events in a predetermined time interval.

7. The system of claim 1, where wherein the quantification of bulbar function for the subject is calculated based on a comparison of the subject's performance at a beginning of the test to the subject's performance at an end of the test.

8. The system of claim 1, wherein the sensor is further configured to capture data of the subject performing a diadochokinetic test of bulbar function.

9. The system of claim 1, wherein the sensor is further configured to capture data of the subject performing a tongue tick rate test of bulbar function.

10. The system of claim 1, wherein the functional quantification of bulbar function is adjusted based at least in part on a demographic characteristic of the subject to obtain an adjusted functional quantification.

11. A method of quantifying bulbar function for a subject, comprising the steps of:
presenting, to the subject, a task testing the subject's bulbar function;
receiving, from a sensor, data of the subject performing the task;
identifying, in the data, a plurality of key events;
calculating, for each key event of the plurality of key events, a quantification for the key event to obtain a respective plurality of key event quantifications;
calculating, for each key event of the plurality of key events, a fatigue effect for the key event to obtain a respective fatigue rate associated with the plurality of key event quantifications,
wherein the plurality of key events are performances of repetitive sensori-motor functions and the plurality of key key event quantifications are measures of the performances of repetitive sensori-motor functions relative to normative values;
determining, based on the plurality of key event quantifications and the fatigue rate, a functional quantification of the subject's bulbar function; and
presenting, to the subject, the functional quantification.

12. The method of claim 11, wherein the task is a tongue tick rate test and each key event of the plurality of key events is an individual tick.

13. The method of claim 11, wherein the task is a diadochokinetic rate test and each key event of the plurality of key events is an individual syllable enunciation.

14. The method of claim 11, further comprising the step of removing, from the plurality of key events, a key event identified as a false positive.

15. The method of claim 11, wherein the functional quantification is compared to a predetermined threshold to diagnose a neurological pathology.

16. One or more non-transitory computer-readable media storing computer-executable instructions that, when executed by a processor, perform a method of quantifying bulbar function for a subject, the method including steps of:
receiving data from a sensor of the subject performing a task testing the subject's bulbar function;
identifying, in the received data, a plurality of key events;
calculating, for each key event of the plurality of key events, a quantification for the key event to obtain a respective plurality of key event quantifications;
calculating, for each key event of the plurality of key events, a fatigue effect for the key event to obtain a respective fatigue rate associated with the plurality of key event quantifications,
wherein the plurality of key events are performances of repetitive sensori-motor functions and the plurality of key key event quantifications are measures of the performances of repetitive sensori-motor functions relative to normative values; and
determining, based on the plurality of key event quantifications and the fatigue rate, a functional quantification of the subject's bulbar function.

17. The media of claim 16, wherein the method further comprises the steps of:
determining, based on the identified key events, an additional rate of key events during an additional predetermined time interval of the task; and
determining the fatigue rate for the subject's bulbar function based on the rate of key events during the predetermined time interval and the additional rate of key events during the additional predetermined time interval.

18. The media of claim 16, wherein the step of receiving data from a sensor of the subject performing a task further comprises receiving data from a plurality of sensors of the subject performing the task.

19. The media of claim 16, wherein the sensor is a microphone.

20. The media of claim 19, wherein the task is a tongue tick rate test.

\* \* \* \* \*